(12) United States Patent
Thorpe et al.

(10) Patent No.: US 10,456,090 B2
(45) Date of Patent: Oct. 29, 2019

(54) METHOD TO DETERMINE INDIVIDUALIZED INSULIN SENSITIVITY AND OPTIMAL INSULIN DOSE BY LINEAR REGRESSION, AND RELATED SYSTEMS

(71) Applicant: Bigfoot Biomedical, Inc., Milpitas, CA (US)

(72) Inventors: Dayton Gray Thorpe, Berkeley, CA (US); Jonathan S. Landy, Berkeley, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 217 days.

(21) Appl. No.: 14/947,347

(22) Filed: Nov. 20, 2015

(65) Prior Publication Data

US 2016/0162797 A1    Jun. 9, 2016

Related U.S. Application Data

(60) Provisional application No. 62/083,191, filed on Nov. 22, 2014.

(51) Int. Cl.
*A61B 5/00* (2006.01)
*A61B 5/145* (2006.01)

(52) U.S. Cl.
CPC .......... *A61B 5/742* (2013.01); *A61B 5/14532* (2013.01); *A61B 5/4839* (2013.01); *A61B 5/7275* (2013.01)

(58) Field of Classification Search
CPC ................ A61B 5/14532; A61B 5/7275
See application file for complete search history.

(56) References Cited

U.S. PATENT DOCUMENTS

| | | | |
|---|---|---|---|
| 7,695,434 B2 | 4/2010 | Malecha | |
| 9,076,107 B2 | 7/2015 | Cameron et al. | |
| 2005/0192494 A1* | 9/2005 | Ginsberg | A61M 5/1723 600/365 |
| 2011/0160555 A1 | 6/2011 | Reifman et al. | |
| 2013/0338453 A1* | 12/2013 | Duke | A61B 5/7282 600/309 |
| 2013/0345663 A1* | 12/2013 | Agrawal | A61M 5/1723 604/503 |

(Continued)

OTHER PUBLICATIONS

Centers for Disease Control and Prevention, Number (in Millions) of Adults with Diabetes by Diabetes Medication Status, United States, 1997-2011, http://www.cdc.gov/diabetes/statistics/meduse/fig1.htm, 2013.

(Continued)

*Primary Examiner* — Kristen Matter
(74) *Attorney, Agent, or Firm* — TraskBritt

(57) ABSTRACT

This invention relates to a method and a device for predicting the glucose concentration of a subject and recommending therapeutic action. The responses of the user's glucose to administered doses of insulin, dietary carbohydrates, and other factors influencing glucose concentration are measured individually for a given user. Once these responses are learned as a function of time, the method and device can receive information about the factors which that have been recently or will soon be administered and can recommend which other factors should also be administered.

21 Claims, 1 Drawing Sheet

(56) References Cited

U.S. PATENT DOCUMENTS

2014/0039383 A1* 2/2014 Dobbles .............. A61B 5/14532
604/66
2014/0073892 A1 3/2014 Randloev et al.
2017/0242975 A1* 8/2017 Kahlbaugh ......... G06F 19/3437
2017/0316592 A1* 11/2017 Kamath ............... A61B 5/0002

OTHER PUBLICATIONS

JDRF, Statistics: JDRF and Diabetes, http://jdrf.org/about-jdrf/fact-sheets/jdrf-anddiabetes-statistics/, 2014.

* cited by examiner

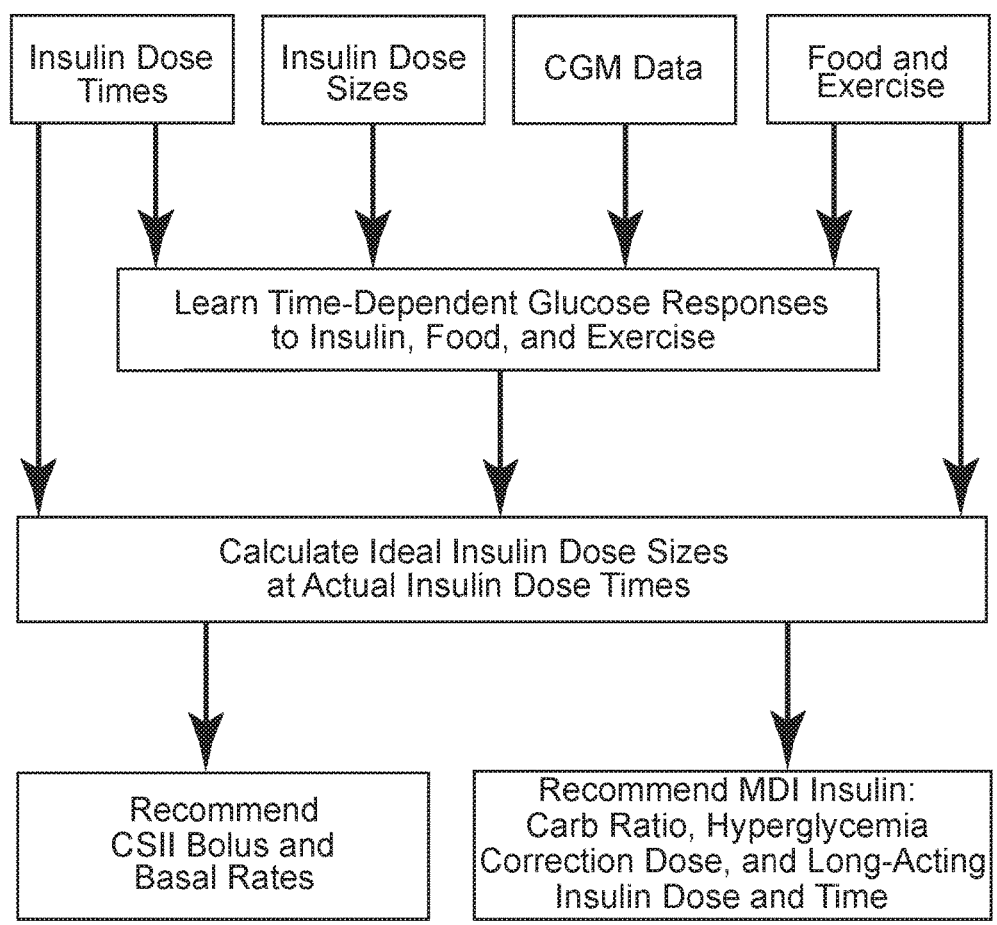

METHOD TO DETERMINE INDIVIDUALIZED INSULIN SENSITIVITY AND OPTIMAL INSULIN DOSE BY LINEAR REGRESSION, AND RELATED SYSTEMS

CROSS-REFERENCE TO RELATED APPLICATIONS

This application claims the benefit of Patent Application Ser. No. 62/083,191, titled "Method to Determine Individualized Insulin Sensitivity and Optimal Insulin Dose by Linear Regression," filed Nov. 22, 2014 by the present inventors, which is incorporated by reference. This invention was not made with any government support and the government has no rights in this invention.

TECHNICAL FIELD

The present invention relates to a method for predicting the glucose concentration of a subject and recommending therapeutic action.

BACKGROUND

In the United States, approximately three million people have type 1 diabetes.[1] To treat their condition, these patients depend either on multiple daily injections (MDI) of insulin or continuous subcutaneous insulin injection (CSII) by insulin pumps. Another 26 million people in the United States suffer from type 2 diabetes, many of whom become insulin dependent. In total, nearly six million Americans depend on insulin.[2] For these patients, choosing the correct dose and type of insulin to take, and when to take it, remains a significant challenge. The goal of an insulin regimen is to maintain blood glucose concentration within a narrow range. Chronically high glucose levels, hyperglycemia, leads to severe health problems and premature death. Acute low glucose levels, hypoglycemia, can cause fainting, seizures, and death. Patients on MDI maintain a healthy glucose level by typically taking five to ten injections per day. These may include injection of a long-acting form of insulin before going to sleep and/or after waking, as well as short-acting insulin injections both before and after every meal and snack, with those following meals chosen to correct for prior insufficient doses. In order to make informed dosage decisions, most diabetics today monitor their blood glucose with small blood draws from a finger prick before each injection. An increasing number of diabetics also monitor their glucose using a continuous glucose monitor (CGM), which provides glucose readings with much higher frequency, commonly around once every five minutes. Although it has already been appreciated that this high frequency data can be used to alert users to problematic glucose levels as they arise, the wealth of data provided by these machines has, so far, been underutilized for the challenge of determining optimal insulin doses.

An "artificial pancreas" is a heavily researched future treatment device for diabetes that uses a closed loop between a CGM and an insulin pump. Given frequent, accurate readings from a CGM, the insulin pump should be able to determine, without human intervention, how much insulin to give. This will require the development of an algorithm that can precisely calculate the response of blood glucose to insulin.

Previous inventions in the field of glucose prediction have used the time-series of glucose over a narrow window in the recent past, possibly around 30 minutes, to predict glucose over a similar time frame in the future, without directly accounting for external factors like insulin, dietary carbohydrates, and exercise. The previous inventions also often focus on making universal predictions of insulin response that are not individualized to each patient and they predict a single, time-integrated response rather than response as a function of time.

U.S. Patent Publication No. 2011/0160555 to Reifman, published Jun. 30, 2011, for "Universal models for predicting glucose concentration in humans" "utilizes similarities in the short-term (30 minutes or less) dynamics of glucose regulation in different diabetic individuals to develop a single, universal autoregressive (AR) model for predicting future glucose levels across different patients." This patent does not account for external factors that cause changes in glucose or attempt to learn individualized models for different patients. Similarly, U.S. Pat. No. 9,076,107, issued Jul. 7, 2015, to Cameron et al. for "Neural network for glucose therapy recommendation" uses recent glucose trends to predict future glucose trends, with the model trained on data from multiple patients rather than individualized. U.S. Pat. No. 7,695,434, issued Apr. 13, 2010, to Malecha for "Medical device for predicting a user's future glycemic state" uses CGM data to predict future glycemic state using a Hidden Markov Model and not linear regression. This method does not use information other than the time series of glucose before the moment of prediction to predict future glucose.

U.S. Pat. No. 7,404,796, issued Jul. 29, 2008, to Ginsberg for "System for determining insulin dose using carbohydrate to insulin ratio and insulin sensitivity factor" is a method for finding individualized carbohydrate-to-insulin ratios (CIRs) and insulin sensitivity factors (ISFs). At its greatest level of detail, that method gives the integrated effect of a unit of insulin or a carbohydrate on a user's glucose concentration, and not the effect as a function of time. That method also does not use linear regression.

U.S. Patent Publication No. 2014/0073892, published Mar. 13, 2014, to Jette Randloev et al., for "Glucose predictor based on regularization networks with adaptively chosen kernels and regularization parameters" describes a method for predicting glucose based on data sets that are sparsely sampled in time, which does not make use of the glucose time series data made available by CGMs and the insulin time series data made available by insulin pumps. That method uses regularization networks with adaptively chosen kernels and regularization parameters and not linear regression.

BRIEF SUMMARY

This patent is for a linear regression-based method to learn a user's blood glucose response to short-acting insulin, long-acting insulin, dietary carbohydrates, and lifestyle factors such as exercise. This method learns a unique response for each user. The calculated response curve is a function of time, not merely the total time-integrated effect of 1 unit of a given factor. After obtaining these response functions, in a second step, this method determines optimal insulin dosages in response to the user's relevant activities. This separate step allows the method to assign an asymmetrical cost function for hyperglycemia and hypoglycemia. This asymmetry is necessary because a positive fluctuation that results in only mild hyperglycemia and no immediate problems could, if only the sign of the fluctuation were reversed, cause severe hypoglycemia and death: Including this information in the same step as learning the user's response to insulin and carbohydrates would distort the user's true response. From the time series of a given user's glucose, insulin, exercise, and carbohydrate intake, the method learns the optimal dose and time of long-acting insulin, the optimal ratio of short-acting insulin to dietary carbohydrates, the optimal correction dose of short-acting insulin for hyperglycemia, and the typical effect of exercise on the user's blood glucose.

The two steps, learning the user's response curves and suggesting the optimal insulin dose, can be decoupled. Once the time dependent response curves are calculated, they can be integrated to determine the cumulative effect of each kind of insulin and dietary carbohydrates. The insulin:carb ratio can then be calculated as the total effect of 1 unit of insulin divided by the total effect of 1 carbohydrate. Alternatively, clinically averaged response functions from many patients, in combination with the user's weight, can be used as an approximate input for the second step, determining the optimal insulin dose.

BRIEF DESCRIPTION OF THE DRAWINGS

FIG. 1 is a flow diagram depicting the input and output to the two stages of the process of determining individualized insulin sensitivity and optimal insulin dose.

DETAILED DESCRIPTION

Step 1 of the method linearly regresses changes in glucose over possibly overlapping time intervals onto the following equation:

$$\Delta g_{i,j} = (EGP_0 - P*g_i)*\Delta t_{i,j} + RGC + \sum_{j=1}^{N_{short}} \theta_{short,j} S_j + \sum_{j=1}^{N_{long}} \theta_{long,j} L_j + \sum_{j=1}^{N_{carb}} \theta_{carb,j} C_j$$

where, $g_i$ is the $i^{th}$ glucose measure in time, $\Delta g_{i,j} = g_{i+j} - g_i$, $\Delta t_{i,j} = t_{i+j} - t_i$, $EGP_0$ is endogenous glucose production extrapolated in 0 glucose, a fit parameter; p is suppression of endogenous glucose production, a fitting parameter;

$RGC = A(g_i - g_{RGC})$ if $g > g_{RGC}$ and $RGC=0$ otherwise, represents renal glucose clearance where A and $g_{RGC}$—the renal glucose clearance threshold—are fit parameters;

$\theta_{short,j}$ are responses to short-acting insulin doses $S_j$ administered j time periods before $t_i$, where each time period could be 30 to 60 minutes, are fit parameters;

$\theta_{long,j}$ are responses to long-acting insulin doses $L_j$ administered j time periods before $t_i$, where each time period could be 30 to 60 minutes, are fit parameters; and $\theta_{carb,j}$ are responses to dietary carbohydrates $C_j$ administered j time periods before $t_i$, where each time period could be 15 to 60 minutes, are fit parameters.

As another example linear-fit form, step 1 of the method could fit glucose changes to the following equation:

$$\Delta g_{i,j} = (EGP_0 - p*g_i)*\Delta t_{i,j} + RGC + \sum_{j=1}^{N_{short}} \sum_{k=0}^{d_{short}} \theta_{short,k}(t_i - t_{short,j})^k S_j +$$

$$\sum_{j=1}^{N_{long}} \sum_{k=0}^{d_{long}} \theta_{long,k}(t_i - t_{long,j})^k L_j + \sum_{j=1}^{N_{carb}} \sum_{k=0}^{d_{carb}} \theta_{carb,k}(t_i - t_{carb,j})^k C_j$$

where, $S_j$ are doses of short-acting insulin taken within some timeframe of $t_i$, possibly 6 hours;

$L_j$ are doses of long-acting insulin taken within some timeframe of $t_i$, possibly 24 hours;

$C_j$ are dietary carbohydrates eaten within some timeframe of $t_i$, possibly 3 hours; and $d_{short}$, $d_{long}$, $d_{carb}$ are the degrees of polynomial response functions.

For any linear-fit form, the length of the time periods for the response curves in step 1 is chosen such that the rate of change of glucose to that factor has an insignificant fluctuation over the time period. The number of time periods to look back from each $g_i$—which could be different for each factor—is chosen such that the number of periods multiplied by the length of each period is longer than the time for the insulin, carbohydrate, or exercise to clear the body. Endogenous glucose production could also be set as a separate factor for different times of day, possibly blocks of one to six hours.

In step 2, the method could use the response functions learned in step 1 to suggest appropriate insulin doses. The output could be carbohydrate ratios, correction doses, and long-acting insulin doses for a user on MDI, or basal and bolus rates for CSII, to be programmed manually in an existing open-loop pump system or to be set automatically in a future, closed-loop artificial pancreas. The method takes the actual time series of food and exercise and combines them with the times, but not the sizes, of actual insulin doses, as well as the response functions to these factors learned in step 1. The method then calculates optimal insulin doses for each relevant event, where the ideal dose is the one that minimizes a cost function that penalizes hyperglycemia and hypoglycemia. The cost function for excursions outside the optimal glucose range could be asymmetrical in order to avoid hypoglycemia more strongly than hyperglycemia. By then averaging over dose size per carbohydrate at each meal, the method can be used to suggest a best insulin:carb ratio. Similarly, by averaging over the ideal correction dose for a given glucose level at each episode of hyperglycemia, the method can suggest the proper correction dose for different levels of hyperglycemia. Step 2 will also assume that a fixed amount of long-acting insulin is taken each day, and it can suggest its ideal dose and time of application.

REFERENCES

[1] JDRF, *Statistics: JDRF and Diabetes*, (2014)
[2] Centers for Disease Control and Prevention, *Number (in Millions) of Adults with Diabetes by Diabetes Medication Status, United States*, 1997-2011, (2013)

The invention claimed is:
1. An insulin delivery system, comprising:
   an insulin delivery mechanism; and
   an insulin delivery control system comprising a memory and a processor operatively coupled to the memory, wherein the processor is configured to:
      store data associated with a user of the insulin delivery system, the data comprising glucose concentration measurements, insulin dosing information, and dietary carbohydrate information;

determine rates of change of glucose concentrations responsive to the glucose concentration measurements;

train a first learned time-dependent glucose response model responsive to the rates of change of glucose concentrations and the insulin dosing information;

train a second learned time-dependent glucose response model responsive to the rates of change of glucose concentrations and the dietary carbohydrate information;

receive a time series of dietary carbohydrate intake;

determine glucose responses over a period of time using the first learned time-dependent glucose response model, the second learned time-depend glucose response model, the time-series of dietary carbohydrate intake, and a number of time series of insulin doses;

integrate the glucose responses over the period of time to determine total glucose responses;

determine a time series of insulin doses of the number of time series of insulin doses that minimizes total glucose responses associated with hyperglycemia and hypoglycemia; and configure the insulin delivery system to provide insulin doses from the insulin delivery mechanism responsive to the determined time series of insulin doses.

2. The insulin delivery system of claim 1, wherein the processor is configured to determine the time series of insulin dose that minimizes total glucose responses associated with hyperglycemia and hypoglycemia by determining an insulin dose amount at a first time responsive to an insulin dose total glucose response, a dietary carbohydrate total glucose response, and a cost function, wherein the cost function penalizes hyperglycemia and hypoglycemia.

3. The insulin delivery system of claim 2, wherein the insulin dose total glucose response is associated with a first insulin dose event at the first time, and the dietary carbohydrate total glucose response is associated with a first dietary carbohydrate intake event at the first time, wherein the first dietary carbohydrate intake event comprises a dietary carbohydrate amount.

4. The insulin delivery system of claim 1, wherein the processor is further configured to determine an insulin-to-carbohydrate ratio by:

determining a time series of dietary carbohydrate intake events, wherein each dietary carbohydrate intake event comprises a dietary carbohydrate amount;

determining a time series of insulin dose events;

determine insulin doses for each of the insulin dose events, wherein each insulin dose of the insulin doses minimizes a risk of blood glucose concentration being outside a target range;

determining dietary carbohydrate total blood glucose responses for the dietary carbohydrate intake events of the time series of dietary carbohydrate intake events;

averaging the dietary carbohydrate total blood glucose responses; and averaging the insulin doses.

5. The insulin delivery system of claim 1, wherein the insulin delivery system is further configured to determine a correction dose.

6. The insulin delivery system of claim 1, wherein the insulin delivery system is further configured to determine a basal dose and a bolus dose.

7. The insulin delivery system of claim 1, further comprising a continuous glucose monitor operatively coupled to the insulin delivery system and configured to provide the glucose concentration measurements to the insulin delivery system, wherein the continuous glucose monitor and insulin delivery system form a closed-loop.

8. The insulin delivery system of claim 1, wherein the insulin dosing information comprises an injected insulin amount, an injected insulin type, and a time of injection.

9. The insulin delivery system of claim 8, wherein the injected insulin type is selected from a group consisting essentially of: short-acting insulin and long-acting insulin.

10. The insulin delivery system of claim 1, wherein the carbohydrate information comprises a dietary carbohydrate amount and a time of consumption of the dietary carbohydrate amount.

11. The insulin delivery system of claim 1, wherein the glucose responses are associated with overlapping time intervals.

12. The insulin delivery system of claim 1, wherein each glucose response of the glucose responses is associated with a timeframe and the timeframe is within a time interval.

13. The insulin delivery system of claim 1, wherein the processor is further configured to:

store data comprising exercise information, wherein the exercise information comprises a type of exercise and an exercise duration; and determine a total glucose response responsive to the exercise information.

14. The insulin delivery system of claim 1, wherein the insulin delivery system is an artificial pancreas.

15. The insulin delivery system of claim 1, wherein the insulin delivery mechanism is a multiple dose injection device.

16. The insulin delivery system of claim 1, wherein the insulin delivery mechanism is an insulin pump.

17. A method, comprising:

storing data associated with a user of an insulin delivery system, the data comprising glucose concentration measurements, insulin dosing information, and dietary carbohydrate information;

determining rates of change of glucose concentration responsive to the glucose concentration measurements;

training a first learned time-dependent glucose response model responsive to the rates of change of glucose concentrations and the insulin dosing information;

training a second learned time-dependent glucose response model responsive to the rates of change of glucose concentrations and the dietary carbohydrate information;

receiving a time series of dietary carbohydrate intake;

determining glucose responses over a period of time using the first learned time-dependent glucose response model, the second learned time-depend glucose response model, the time-series of dietary carbohydrate intake, and a number of time series of insulin doses;

integrating the glucose responses over a period of time to determine total glucose responses;

determining a time series of insulin doses of the number of time series of insulin doses that minimizes total glucose responses associated with hyperglycemia and hypoglycemia and configuring the insulin delivery system to provide insulin doses from an insulin delivery mechanism responsive to the determined time series of insulin doses.

18. The method of claim 17, wherein the determining the time series of insulin doses that minimizes total glucose responses associated with hyperglycemia and hypoglycemia comprises: determining an insulin dose amount at a first time responsive to an insulin dose total glucose response, a dietary carbohydrate total glucose response, and a cost function, wherein the cost function penalizes hyperglycemia and hypoglycemia.

19. The method of claim 18, wherein the insulin dose total glucose response is associated with a first insulin dose event at the first time, and the dietary carbohydrate total glucose response is associated with a first dietary carbohydrate intake event at the first time, wherein the first dietary carbohydrate intake event comprises a dietary carbohydrate amount.

20. The method of claim 17, further comprising:
determining a time series of dietary carbohydrate intake events, wherein each dietary carbohydrate intake event comprises a dietary carbohydrate amount;
determining a time series of insulin dose events;
determine insulin doses for each of the insulin dose events, wherein each insulin dose of the insulin doses minimizes a risk of blood glucose concentration being outside a target range;
determining dietary carbohydrate total blood glucose response for the dietary carbohydrate intake events of the time series of dietary carbohydrate intake events;
averaging the dietary carbohydrate total blood glucose responses; and
averaging the insulin doses.

21. The method of claim 17, wherein the insulin delivery mechanism is an insulin pump or a multiple injection device.

* * * * *

UNITED STATES PATENT AND TRADEMARK OFFICE
CERTIFICATE OF CORRECTION

PATENT NO. : 10,456,090 B2
APPLICATION NO. : 14/947347
DATED : October 29, 2019
INVENTOR(S) : Dayton Gray Thorpe and Jonathan S. Landy Page 1 of 1

It is certified that error appears in the above-identified patent and that said Letters Patent is hereby corrected as shown below:

On the Title Page
In ITEM (57) Abstract, Line 10:    change "factors which that" to --factors that--

Signed and Sealed this
Thirty-first Day of December, 2019

Andrei Iancu
*Director of the United States Patent and Trademark Office*